United States Patent
Munoz et al.

(10) Patent No.: US 10,688,141 B2
(45) Date of Patent: Jun. 23, 2020

(54) PROBIOTIC BEVERAGE CONTAINING LIVING MYCELIUM AND METHOD OF PRODUCTION

(71) Applicant: Mycotea, LLC, Vero Beach, FL (US)

(72) Inventors: Alfred M. Munoz, Port St Lucie, FL (US); Giuliano P. Melluso, Ft Pierce, FL (US)

(73) Assignee: MYCOTEA, LLC, Vero Beach, FL (US)

( * ) Notice: Subject to any disclaimer, the term of this patent is extended or adjusted under 35 U.S.C. 154(b) by 939 days.

(21) Appl. No.: 14/515,518

(22) Filed: Oct. 16, 2014

(65) Prior Publication Data

US 2016/0106791 A1   Apr. 21, 2016

(51) Int. Cl.

| | |
|---|---|
| *A61K 36/062* | (2006.01) |
| *A61K 36/07* | (2006.01) |
| *A61K 36/06* | (2006.01) |
| *A23L 2/52* | (2006.01) |
| *A23L 33/125* | (2016.01) |
| *A23L 31/00* | (2016.01) |
| *A23L 2/60* | (2006.01) |
| *A23L 2/56* | (2006.01) |
| *A23L 33/135* | (2016.01) |

(52) U.S. Cl.
CPC .......... *A61K 36/06* (2013.01); *A23L 2/52* (2013.01); *A23L 2/56* (2013.01); *A23L 2/60* (2013.01); *A23L 31/00* (2016.08); *A23L 33/125* (2016.08); *A23L 33/135* (2016.08); *A23V 2002/00* (2013.01); *A61K 2236/19* (2013.01)

(58) Field of Classification Search
None
See application file for complete search history.

(56) References Cited

U.S. PATENT DOCUMENTS

2016/0304924 A1* 10/2016 Fortin .................... A23B 7/105

OTHER PUBLICATIONS

Henkel, (2005) Mycologia 97(1): pp. 1-11. (Year: 2005).*
Mizuno et al. (1995) Food Reviews International vol. 11, Issue 1, pp. 69-81. (Year: 1995).*
Cukalovic et al. (2010) Food Research International, 43: 2262-2269. (Year: 2010).*
Henkel (2004) Economic Botony 58(1): 25-37. (Year: 2004).*
Lei et al. (2004) J. Applied Microbiology 96, 384-397. (Year: 2004).*
Website document entitled: "Liquid Culture and Live Spawn" (available at http://www.mushbox.co/Liquid-Culture-and-Live-Spawn_b_4.html). Posted Jan. 1, 2011. Downloaded from website: Jan. 22, 2018. (Year: 2011).*
Marsh et. al. (2013) PLoS ONE 8(7): e69371. (Year: 2013).*
Marsh et al. (2014) Trends in Food Science & Technology, vol. 38, Issue 2, pp. 113-124.*
Muyanja et al. (2003) African Journal of Food, Agriculture, Nutrition and Development, vol. 3, No. 1 pp. 10-19. (Year: 2003).*
Ben Omar et al. (2000) Applied and Environmental Microbiology, vol. 66, No. 9, pp. 3664-3673. (Year: 2000).*
Yamamoto et al. (2011) Food Sci. Technol. Res., 17(3): 209-218. (Year: 2011).*
Yang et al. (1998) Process Biochemistry, vol. 33, No. 5, pp. 547-553. (Year: 1998).*
Yang et al. (2009) Food Chemistry 112 pp. 1-5. (Year: 2009).*

* cited by examiner

*Primary Examiner* — Russell G Fiebig
(74) *Attorney, Agent, or Firm* — King & Spalding

(57) ABSTRACT

Humans have utilized mushrooms and mycelium for thousands of years. Currently mycelium is consumed at large in the form of dried powders in supplements. This patent describes a method for preparing a probiotic beverage containing living mycelium. This method allows the delivery of living mycelium through a water-sweetener-flavor base. Due to the living form of the mycelium and the consumable substrate this method is able to provide the beneficial properties of mycelium without degradation of the mycelium's beneficial properties.

12 Claims, 3 Drawing Sheets

FIGURE 1.A
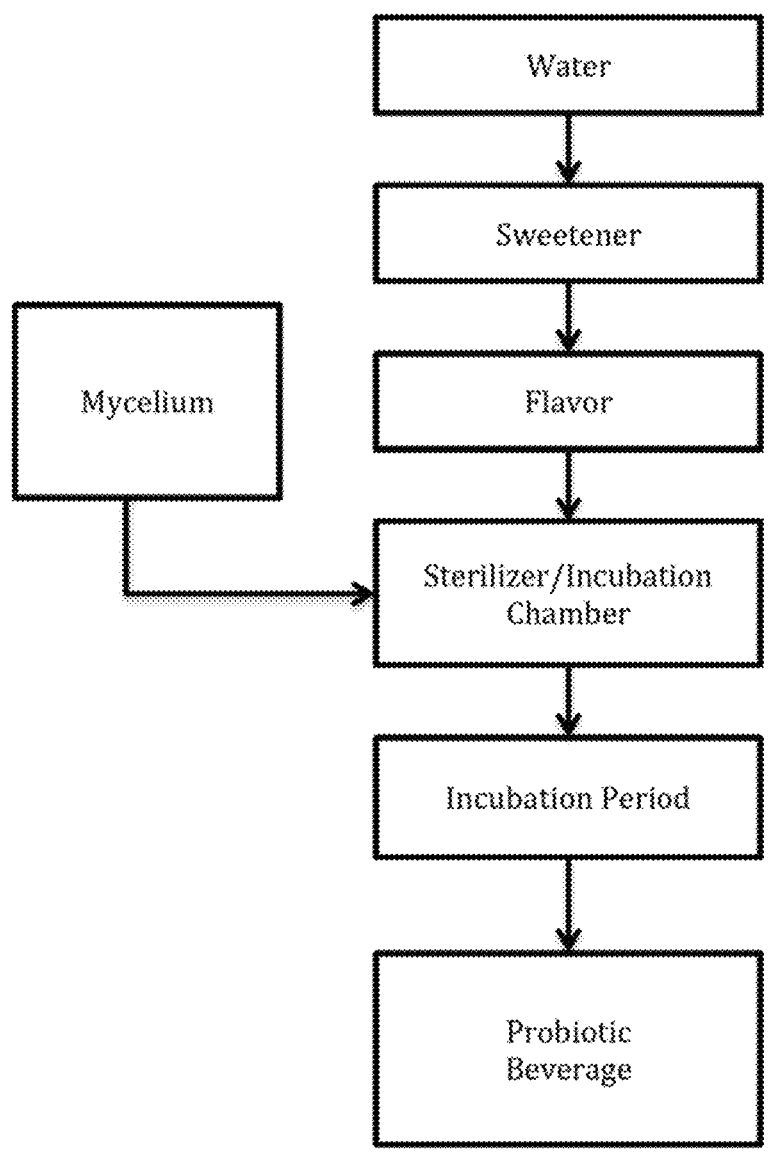

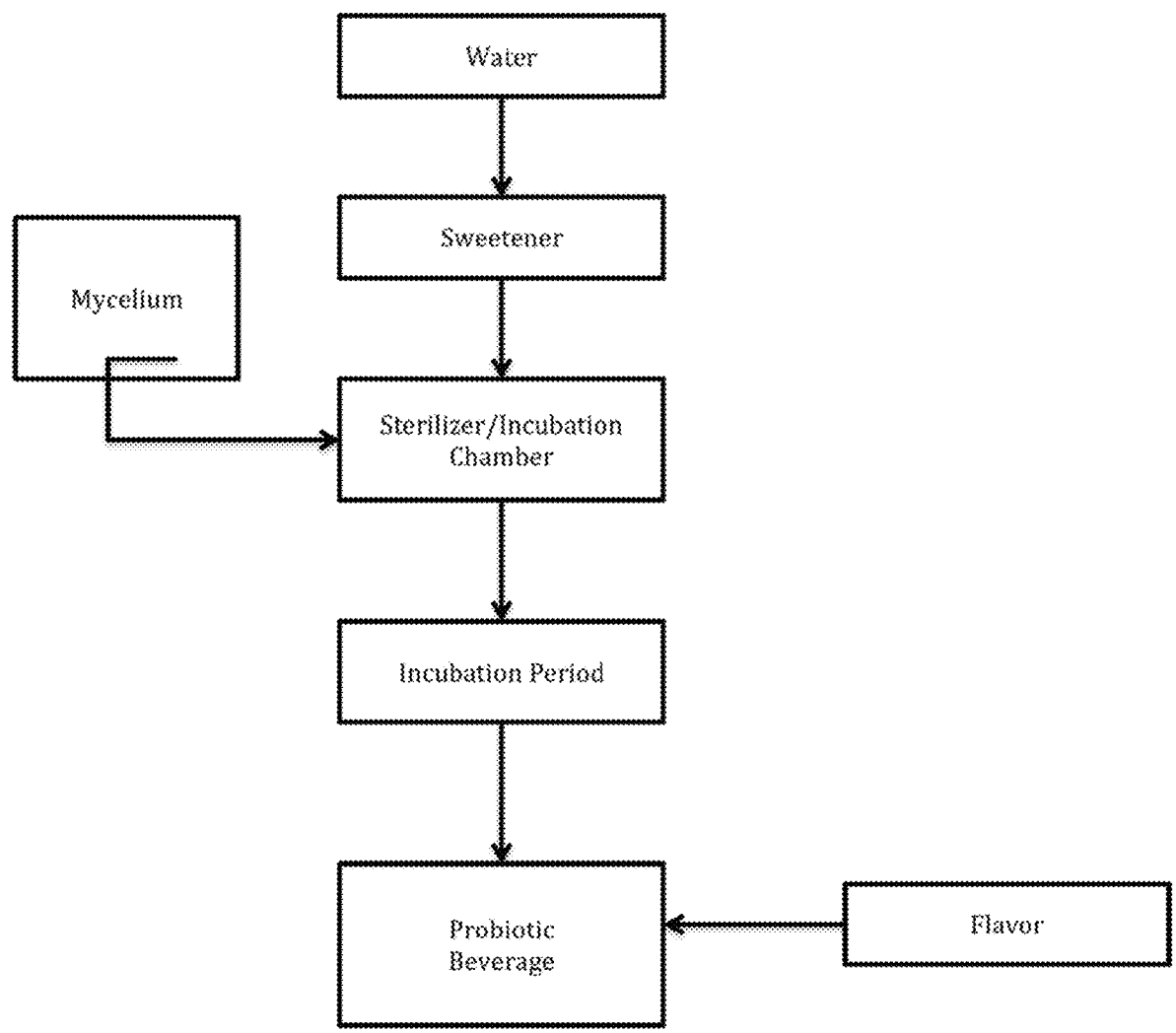
FIGURE 1.B

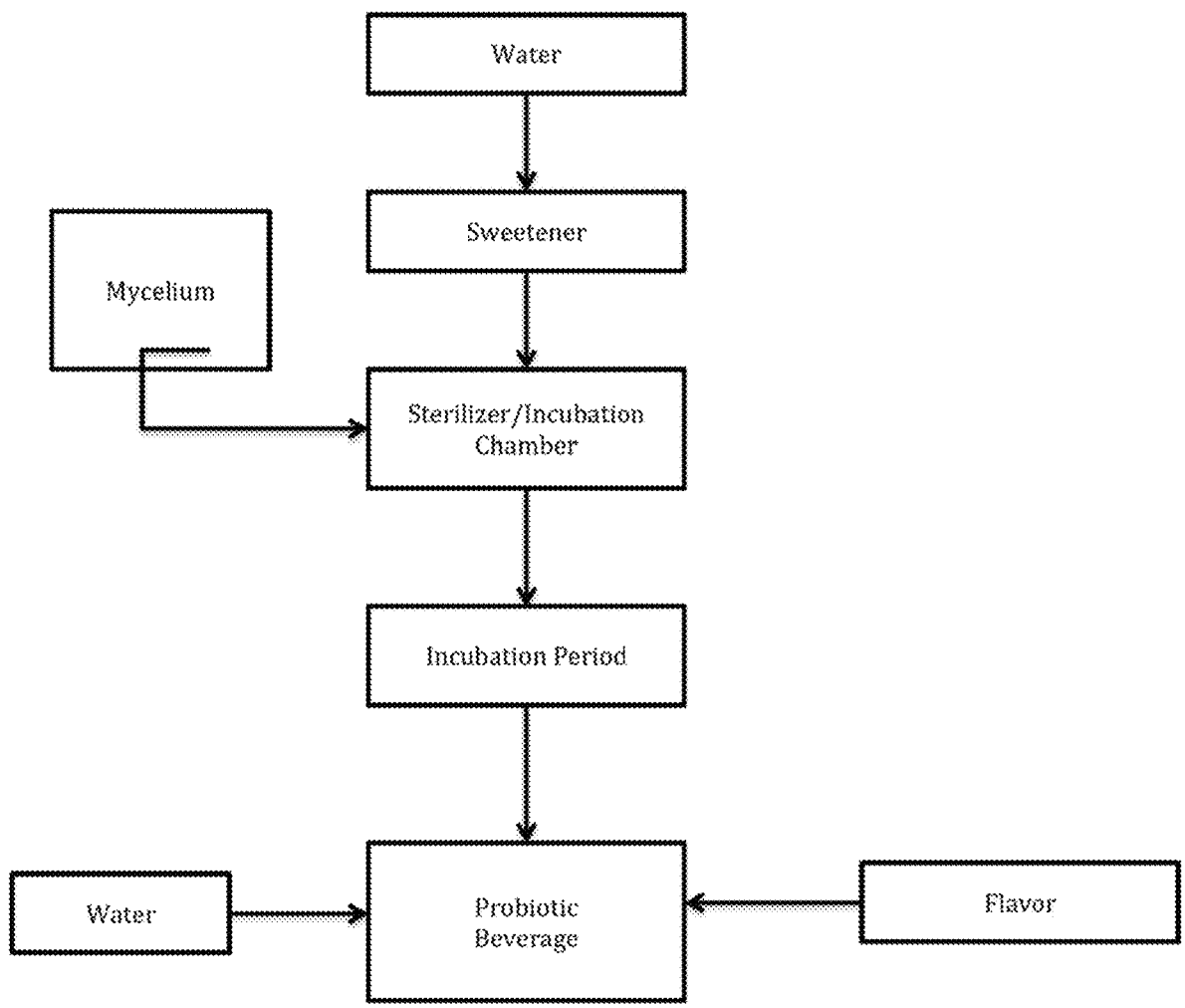

PROBIOTIC BEVERAGE CONTAINING LIVING MYCELIUM AND METHOD OF PRODUCTION

FIELD OF THE INVENTION

The present invention relates generally to beverages and the preparation of probiotic beverages. More particularly, the invention pertains to methods for preparing a probiotic beverage containing living mycelium.

BACKGROUND OF THE INVENTION

Health-conscious consumers have been the driving force behind a continual increase in the production and sale of nutritional and probiotic beverages, supplements, vitamins, fruit and vegetable extracts, and the like. During the past decade, consumer appeal has shifted towards wellness drinks of a raw, organic and balanced nature. However, most commercial beverages do not provide or supply significant vitamins, antioxidants, proteins, amino acids, complex carbohydrates, antiviral, antibiotic and antitumor agents. Instead, many beverages intended to promote health improvement, wellbeing, energy and athleticism, are filled with artificial flavorings and colorings, which have been shown to have adverse effects on the human body. More recently, there has been increasing consumer awareness of the health benefits of naturally occurring fungi known as mycelium.

More accurately, mycelium is the vegetative part of a fungus, consisting of a mass of branching, thread-like hyphae. Fungal colonies composed of mycelium are found in and on soil and many other substrates. It is well known that mycelium is vital in terrestrial and aquatic ecosystems for its ability to decompose plant plant material. Mycelium contribute to the organic fraction of soil, and their growth releases carbon dioxide back into the atmosphere. Furthermore, some types of mycelium are known to increase the efficiency of water and nutrient absorption of most plants and confer resistance to some plant pathogens. Mycelium is an important food source for many organisms due to its high nutritional value.

Mushrooms, the fruit of Mycelium, have been revered for thousands of years by practitioners of traditional Asian medicine. The benefits of mushrooms consist of but are not limited to potent antioxidants, the ability to stimulate immune function in the human body, as well as stimulate metabolism, regrowth of nerves, anti-inflammatory properties, hypertension reducer and cholesterol reducer. To sum up mushrooms are documented as a true cure all. Mycelium is the primary source of the beneficial properties of mushrooms. Primarily, mycelium products are available for consumption as extracts of mycelium or powdered combinations of dried mycelium harvested from liquid culture or solid substrate cultures. However, there is complete lack of availability of consumable products delivering raw living mycelium in the form of a probiotic beverage.

Accordingly, there remains a need in the art for a method of producing a probiotic beverage incorporating mycelium in a raw live form, as opposed to a mycelium culture to harvest or an extract. That is, there is a need for such a product that is not intended for further inoculation of a substrate, as is the case during the production of spawn, inoculation slurry or mother culture. It would be desirable to provide such a method wherein the mycelium base is combined with water and flavoring to provide a final probiotic beverage. It would be further desirable to provide such live mycelium wherein further colonization of substrate is limited by temperature-related dormancy, as opposed to known methods that incorporate sterilization steps after inoculation, thereby killing the mycelium. It would be desirable to provide such a process that does not require separation or filtering of mycelium from the substrate, for subsequent insertion into a drink. It would be further desirable to provide a universal process that is not "species specific," instead functioning with any *Basidiomycota* or *Ascomycota* fungi, and can be incorporated with bacteria or algae or any organism in the kingdom Monera. Preferably, the method would not be geared toward producing a specific molecule found within mycelia, but instead utilizing all proteins, polysaccharides and enzymes naturally occurring in the mycelium. Preferably, the method would incorporate the use of sugars and nectars as a nutrient base, as opposed to grain washes, grain broths, vinegar and the like. Finally, it would be desirable to provide such a process that avoids the use of an extraction process, such as hot water extraction, such that there is no separation of the mycelium from the liquid substrate.

BRIEF DESCRIPTION OF THE DRAWINGS

FIG. 1.A shows the route of production of a probiotic beverage where the water, sweetener and flavor are combined into a sterilizer/incubation chamber, example would be a bioreactor, and is then sterilized. After the water, sweetener and flavor are sterilized, mycelium is introduced into the chamber and the mixture is incubated until desired mycelium density is achieved. After incubation the probiotic beverage is finalized.

FIG. 1.B shows the route of production of a probiotic beverage where the water and sweetener is combined into a sterilizer/incubation chamber, example would be a bioreactor, and is then sterilized. After the water and sweetener are sterilized, mycelium is introduced into the chamber and the mixture is incubated until desired mycelium density is achieved. After incubate period, the probiotic beverage is completed by the combination of a sterilized flavor base with the mycelium sweetener water solution.

FIG. 1.C shows the route of production of a probiotic beverage where the water and sweetener is combined into a sterilizer/incubation chamber, example would be a bioreactor, and is then sterilized. After the water and sweetener are sterilized, mycelium is introduced into the chamber and the mixture is incubated until desired mycelium density is achieved. After incubate period, the probiotic beverage is completed by the combination of a sterilized flavor base and the mycelium sweetener solution with water.

DETAILED DESCRIPTION

The following detailed description is merely exemplary in nature and is not intended to limit the described embodiments or the application and uses of the described embodiments. As used herein, the word "exemplary" or "illustrative" means "serving as an example, instance, or illustration." Any implementation described herein as "exemplary" or "illustrative" is not necessarily to be construed as preferred or advantageous over other implementations. All of the implementations described below are exemplary implementations provided to enable persons skilled in the art to make or use the embodiments of the disclosure and are not intended to limit the scope of the disclosure, which is defined by the claims.

(a) Sterilization of beverage preparation area;

(b) Sterilization of beverage preparation equipment;

(c) Provide a volume of distilled, reverse osmosis, city tap water, spring water, or a sterilized volume of water into beverage production equipment;

(d) Optionally, heat water to a temperature of approximately 200° F., particularly where it is desired to facilitate faster combination with sweetener;

(e) Introduce sweetener or nectar into volume of heated water at a preferred ratio of approximately 3 percent (by volume) of sweetener to water, creating sweetener-water solution. Agave is the preferred sweetener and base for mycelia metabolism; however, agave or any of the named sweetener bases can be added/introduced at a ratio within the range of 1 percent to 35 percent (by weight) of sweetener to water;

(f) Introduce flavoring additive, preferably dried tea material, into agave-water solution at a preferred ratio of 5 g tea to 500 ml solution, to produce substrate (Alternatively, artificial flavors, natural flavors, herbs, extracts, juices, juice concentrate and the like, may be used in lieu of or in addition to tea, in which case the preferred ratio of flavor/concentrate of the sweetener-water solution would fall within a range of 0.5 percent to 80.5 percent flavor/concentrate (by weight). Where dried tea material is used, it may be incorporated as cold brew or a heated brew. These brewing and steeping steps/techniques could be performed within a temperature range of 0 to 100 degrees Celsius. Furthermore, brewing may be conducted under pressure, in which case it is contemplated that brewing and steeping steps/techniques could be performed within a temperature range having a maximum temperature of approximately 200 degrees Celsius. While tea flavoring is preferred, it will be apparent to those skilled in the art that it is not necessary to carry out the present method. Furthermore, any aforementioned contemplated flavorings and additions can be introduced within the temperature ranges stated above vis-à-vis tea. Depending upon the production temperature chosen, sterilization or pasteurization can be achieved during brewing;

(g) Brew flavored substrate until a desired flavoring is achieved;

(h) Filter to remove suspended solids if necessary;

(i) After the step of filtering out the suspended solids, the remaining solution is preferably sterilized by use of a bioreactor. A bioreactor is the preferred method because of its ability to sterilize and control temperature during mycelium cultivation. The bioreactor also aids in agitation of liquid which speeds mycelium growth. Alternatively sterilization can be achieved by a combination of methods, such as microfiltration and UV sterilization. In this case, microfiltration is preferably accomplished using filter membranes having a pore size within a range of one 1 to 1,000 nanometers (nm), and UV sterilization utilizing wave lengths within a range of 10 nm to 500 nm, and more preferably within a range of 250 nm to 280 nm, which, through experimentation we have found produces peak germicidal effect. Sterilization or pasteurization can be performed with heat at aforementioned standard temperatures and time intervals. Furthermore, as will be apparent to those skilled in the art, tindalization (alternatively spelled "tyndallization") could theoretically be used as an effective sterilization technique. Tyndallization essentially consists of heating a substance for 15 minutes for three consecutive days (usually by boiling it). On the second day, most of the spores that survived the first day will have germinated into bacterial cells. The second day's heating will kill these cells. The third day kills bacterial cells from late germinating spores. During the waiting periods over the three days, the substance being sterilized is kept at a warm room temperature (i.e., a temperature that is conducive to germination of the spores). During this step of the process, for example, a fermenter could be used to hold the liquid substrate, the liquid substrate subsequently passed through a UV sterilization unit, and into a sterilized fermenter for inoculation with mycelium. Alternatively, the UV sterilization unit could be replaced with a microfiltration unit or used in conjunction therewith. The most preferred implementation would be the use of a bioreactor to achieve sterilization;

(j) Once flavor-sweetener-water solution is sterilized in the bioreactor, mycelium is then introduced at a preferred ratio of 10% mycelium/volume of flavor-sweetener-water solution. The range for the amount of mycelium added can be 1% to 62% by volume. This will alter the mycelium density of the final product.

(k) After addition of mycelium, allow mycelium to incubate at optimal temperature for 3 to 7 days to achieve finished probiotic beverage with desired ratio of mycelium to total beverage volume. (note: incubation temperature and time are dependent upon optimal growth conditions of mycelium species). Incubation preferably occurs within a large bioreactor. However, as will be apparent to those skilled in the art, incubation can occur in virtually any large vessel that is completely sealed and sterilized. Preferably, an optional step of agitation by shaking, spinning, subjecting to an inner rotor, is performed. Accordingly, the most preferred incubation is with the use of a vat having controlled temperature and an inner agitator (i.e., essentially a bioreactor). Sterilization of the incubation vessel can be achieved by known steam or chemical sterilization techniques prior to introduction of the mycelium and base. By way of example, golden oyster mushrooms (or *Pleurotus cintrinopileatus*) have an optimal temperature range of 23.89 to 29.44 degrees Celsius. *Gandoderma lucidum*, or reishi, have an optimal temperature range of 21-27 degrees C. *Cordyceps* show growth from 15 to 35 degrees Celsius. It should be noted that these ranges are not universally agreed upon in the scientific community; however, it is believed that a temperature range of 25 to 30 degrees Celsius is probably optimal for most species. With that said, some strains, such as king oyster strains and some blue oyster strains, are cold weather and will require correspondingly lower temperatures;

(l) After optimal colonization of substrate has accrued, cool substrate to a temperature within the range of approximately 37° F. to 56° F. (2.78 to 13.33 degrees Celsius), to adequately stall the production of mycelium biomass in order to maintain optimum saturation levels. Optional saturation level is completely dependent upon the desired final product, e.g., whether a highly dense viscous product or low density refreshing iced tea drink is desired. In general, optimal saturation levels can fall within a range of 5 to 95 percent mycelium to substrate;

(m) Optionally, the process can be altered by adding different artificial, natural and organic based flavoring, additives such as vitamins, minerals, artificial sweeteners, natural sweeteners, energy-providing herbs, herb extracts, juices, juice concentrates, natural or synthetic caffeine, other forms of energy-providing chemicals, herbs, protein supplements, antioxidants, water sources, etc.

(n) The above-described embodiments are merely exemplary illustrations of implementations set forth for a clear understanding of the principles of the invention. Many variations, combinations, modifications or equivalents may be substituted for elements thereof without departing from the scope of the invention. Therefore, it is intended that the invention not be limited to the particular embodiments disclosed as the best mode contemplated for carrying out this invention, but that the invention will include all the embodiments falling within the scope of the appended claims.

(o) For example, in an alternative implementation the following steps may be incorporated into the procedure: (1) utilize two bioreactors, one that contains liquid mycelium base, and one that contains flavor base; (2) Sterilize both bioreactors and inoculate the one containing the mycelium base, allow the mycelium to colonize over a 3 to 7 day period; (3) Combine product from both bioreactors at a ratio that will allow for desired final probiotic beverage, ex 20% mycelium base to 80% liquid flavor base (note: flavor base and mycelium base can be concentrated and therefore diluted with water to achieve a ready to drink probiotic beverage, preferred combination ratio of but not limited to 20% flavor base to 20% mycelium base to 80% sterilized water); (4) Inoculate liquid with mycelium; (5) Bottle/package final product for sale and consumption.

(p) Furthermore, as will be apparent to those skilled in the art, although the processes described herein have been specifically directed to production of a living mycelium containing probiotic beverage for human consumption, the process is easily adaptable for delivering the beverage to animals by using polysaccharides that don't affect blood sugar and deliver the same health benefits to domestic pets and livestock.

What is claimed is:

1. A method of preparing a beverage containing living mycelia, comprising the steps of:
   (i) introducing a volume of water into sterilized beverage preparation equipment;
   (ii) introducing a sweetener into said water to create a sweetener solution;
   (iii) introducing a flavor additive into said sweetener solution to create a sweetener-flavor-water solution;
   (iv) sterilizing the sweetener-flavor-water solution;
   (v) introducing living mycelia comprising *Basidiomycota* and *Ascomycota* to the sweetener-flavor-water solution to provide mycelia-sweetener-flavor-water solution;
   (vi) incubating the mycelia-sweetener-flavor-water solution for 3 to 7 days at optimal conditions to promote optimal growth of mycelium species; and
   (vii) cooling the mixture of step (vi) to a temperature from about 37° F. to 56° F. to stall the production of mycelium biomass in order to maintain optimum saturation levels, thereby providing a beverage containing living mycelia.

2. The method of claim 1, wherein the sweetener is selected from the group consisting of agave nectar, honey, stevia, corn syrup, high fructose corn syrup, molasses, cane juice, brown rice syrup, glucose, fructose, dextrose, maltose monoglycerides, di-glycerides, maltitol, xylitol, lactitol, sorbitol, sucralose, aspartame, acesulfame K, neotame and saccharin.

3. The method of claim 2, wherein in step (ii) said sweetener is added in an amount falling within a range of 1% to 35% by volume of said sweetener solution.

4. The method of claim 1, further comprising adding at least one of: vitamins, minerals, artificial sweeteners, natural sweeteners, energy-providing herbs, herb extracts, juices, juice concentrates, natural caffeine, synthetic caffeine, protein supplements, carbon dioxide, nitric oxide and antioxidants.

5. The method of claim 1, wherein the flavor additive is selected from the group consisting of dried tea material, artificial flavors, natural flavors, herbs, extracts, juices and juice concentrate.

6. The method of claim 5, wherein the flavor additive is a dried tea material.

7. The method of claim 1, further comprising agitation during step (vi).

8. The method of claim 1, wherein the mycelia comprises *Basidiomycota* and *Ascomycota* mycelia selected from the group consisting of *Pleurotus cintrinopileatus, Ganoderma lucidum, Cordyceps* species, reishi complex, *Ganoderma tsugae, Pleurotus eryngii* and *Pleurotus* var. *columbis.*

9. The method of claim 1, wherein in step (v) the living mycelia is introduced in an amount from about 1% to 62% by volume of the sweetener-flavor-water solution.

10. The method of claim 9, wherein in step (v) the living mycelia is introduced in an amount of about 10% volume of the sweetener-flavor-water solution.

11. The method of claim 1, wherein the mycelia-sweetener-flavor water solution is incubated at a temperature from 15° C. to 35° C.

12. A method of preparing a beverage containing living mycelia, comprising the steps of:
   (i) introducing a volume of water into sterilized beverage preparation equipment;
   (ii) introducing a sweetener into said water to create a sweetener solution;
   (iii) sterilizing the sweetener solution;
   (iv) introducing living mycelia comprising *Basidiomycota* and *Ascomycota* to the sweetener solution to provide mycelia-sweetener-water solution;
   (v) incubating the mycelia-sweetener-water solution for 3 to 7 days at optimal conditions to promote optimal growth of mycelium species;
   (vi) cooling the mixture of step (v) to a temperature from about 37° F. to 56° F. to stall the production of mycelium biomass in order to maintain optimum saturation levels; and
   (vii) introducing a flavor additive to the mixture of step (vi) to provide a beverage containing living mycelia.

* * * * *